United States Patent
Hoy (10) Patent No.: US 9,922,515 B2
(45) Date of Patent: Mar. 20, 2018

(54) SECURITY, MONITORING AND SAFETY SYSTEM WITH CONTAINMENT AND METHOD OF USE

(71) Applicant: Marian Alice Hoy, Johnson City, TX (US)

(72) Inventor: Marian Alice Hoy, Johnson City, TX (US)

( * ) Notice: Subject to any disclaimer, the term of this patent is extended or adjusted under 35 U.S.C. 154(b) by 287 days.

(21) Appl. No.: 14/873,304

(22) Filed: Oct. 2, 2015

(65) Prior Publication Data

US 2017/0098357 A1    Apr. 6, 2017

(51) Int. Cl.
| | |
|---|---|
| G08B 15/02 | (2006.01) |
| G01V 5/00 | (2006.01) |
| G01N 33/00 | (2006.01) |
| H04N 7/18 | (2006.01) |
| G01V 3/00 | (2006.01) |
| E05G 5/00 | (2006.01) |
| E05G 5/02 | (2006.01) |
| G08B 15/00 | (2006.01) |
| E05G 1/026 | (2006.01) |
| E05G 1/024 | (2006.01) |

(52) U.S. Cl.
CPC ............ *G08B 15/02* (2013.01); *E05G 5/003* (2013.01); *E05G 5/02* (2013.01); *G01N 33/0057* (2013.01); *G01V 3/00* (2013.01); *G01V 5/0008* (2013.01); *G08B 15/007* (2013.01); *H04N 7/181* (2013.01); *E05G 1/024* (2013.01); *E05G 1/026* (2013.01)

(58) Field of Classification Search
CPC .... G08B 15/02; G08B 15/007; G01V 5/0008; G01V 3/00; G01N 33/0057; H04N 7/181; E05G 5/003; E05G 5/02; E05G 1/026; E05G 1/024
USPC ...................................................... 109/6, 20
See application file for complete search history.

(56) References Cited

U.S. PATENT DOCUMENTS

| | | | | |
|---|---|---|---|---|
| 1,462,781 A | * | 7/1923 | Babiarz ................... | E05G 7/004 109/14 |
| 1,912,055 A | * | 5/1933 | Young ....................... | F41H 9/04 109/20 |
| 3,759,195 A | | 9/1973 | Hitrys | |
| 3,844,232 A | | 10/1974 | Robinson | |
| 3,965,827 A | | 6/1976 | Reeves | |
| 4,068,780 A | * | 1/1978 | Fegley ....................... | B01J 7/00 109/20 |
| 4,122,783 A | | 10/1978 | Pretini | |
| 4,341,165 A | | 7/1982 | Calandritti | |

(Continued)

FOREIGN PATENT DOCUMENTS

EP     0169095 A1    6/1985

*Primary Examiner* — Suzanne L Barrett (57) ABSTRACT

A safety enclosure, detention, and surveillance system with a walled enclosure with impact resistant walls, an entrance door and exit door located in an inner scanning chamber, a storage chamber located in inner scanning chamber, an x-ray metal detector with a conveyor belt, a walkthrough metal detector, a gas ionization explosives detector, and a weapons depository unit. The inner storage chamber further contains an air conditioning unit and a sedation material unit for storage and release with ports to access the inner scanning chamber by which the sedation dispenser can pump sedation material from the storage chamber into the inner scanning chamber and render a threat incapacitated.

24 Claims, 6 Drawing Sheets

(56) References Cited

U.S. PATENT DOCUMENTS

| | | | |
|---|---|---|---|
| 4,461,221 A | 7/1984 | Schandle | |
| 4,586,441 A | 5/1986 | Zeklch | |
| 4,656,954 A | 4/1987 | Tonall | |
| 4,741,275 A | 5/1988 | Lewiner | |
| 4,841,752 A * | 6/1989 | Fletcher | E05G 1/12 109/20 |
| 4,928,429 A | 5/1990 | Colombo | |
| 5,195,448 A | 3/1993 | Sims | |
| 5,311,166 A | 5/1994 | Frye | |
| 5,600,303 A * | 2/1997 | Husseiny | F41H 11/12 340/568.1 |
| 5,692,446 A * | 12/1997 | Becker | E05G 5/02 109/20 |
| 5,694,867 A | 12/1997 | Diaz-Lopez | |
| 5,881,915 A * | 3/1999 | Smrz | G08B 15/02 109/20 |
| 5,983,578 A | 11/1999 | Huttie | |
| 6,298,603 B1 | 10/2001 | Diaz | |
| 6,308,644 B1 * | 10/2001 | Diaz | E05G 5/003 109/6 |
| 6,348,866 B1 | 2/2002 | Lopez | |
| 6,359,582 B1 | 3/2002 | MacAleese | |
| 6,406,918 B1 * | 6/2002 | Bannister | G01N 25/4866 374/100 |
| 6,472,984 B1 | 10/2002 | Risi | |
| 6,484,650 B1 | 11/2002 | Stomski | |
| 6,686,846 B1 | 2/2004 | Lee | |
| 6,724,304 B2 | 4/2004 | Risi | |
| 6,742,301 B1 * | 6/2004 | Schwarz | E05G 5/003 49/42 |
| 6,745,520 B2 | 6/2004 | Puskaric | |
| 6,972,693 B2 * | 12/2005 | Brown | G01V 5/0008 250/358.1 |
| 7,048,312 B2 | 5/2006 | Brunner | |
| 7,053,785 B2 | 5/2006 | Akins | |
| 7,388,485 B1 * | 6/2008 | Shen | E05G 1/12 109/20 |
| 7,707,951 B1 * | 5/2010 | Prasad | E05G 5/003 109/2 |
| 7,823,338 B2 | 11/2010 | Slagel | |
| 8,269,600 B2 | 9/2012 | Floyd | |
| 2002/0154012 A1 | 10/2002 | Risi | |
| 2005/0237178 A1 | 10/2005 | Slomski | |
| 2007/0200566 A1 * | 8/2007 | Clark | G01V 5/0008 324/318 |
| 2010/0147201 A1 | 6/2010 | Mucio | |
| 2012/0115965 A1 | 5/2012 | Olah et al. | |
| 2016/0282319 A1 * | 9/2016 | Awad | G01N 1/02 |

* cited by examiner

SECURITY, MONITORING AND SAFETY SYSTEM WITH CONTAINMENT AND METHOD OF USE

CROSS-REFERENCE TO RELATED APPLICATIONS

Not applicable.

STATEMENT REGARDING FEDERALLY SPONSORED RESEARCH

Not applicable

BACKGROUND

The present invention, and inventive system, is a new and novel invention that works as security, safety and monitoring system that has the capability to humanely capture potentially threating individuals or small groups. One goal of the present invention is to provide a humane capture and detainment capability of an armed 'threat' by creating a bulletproof and/or bomb proof (walls, floor, ceiling, doors, baffles, and metal frames and hardware) safety structure that is attached to a door or entry way.

The present invention is readily distinguishable for the following prior art:

U.S. Pat. No. 3,759,195 ("'195") to Hitrys is not comparable to the present invention because '195 addresses protecting a guard in a moveable guard station with ropes and pulleys, which is not found or addressed in the present invention. In '195 there are no safety measures for law enforcement to extract the threat from the moveable compartment of '195. '195 also does not reference, or mention, enhanced bulletproof glass that will absorb a round from a high powered weapon. The present invention also contains bomb detection as well as an x-ray lock down box.

U.S. Pat. No. 3,844,232 ("'232") to Robinson is not comparable to the present invention because '232 concerns keeping unauthorized persons from operating a cash register, not entering into a building or walk area. The present invention also contains bomb detection as well as an x-ray lock down box.

U.S. Pat. No. 3,965,827 ("'827") to Reeves is different from the present invention in that '827 focuses on capturing a threat by lowering a floating bulletproof cylinder cage that hangs from the ceiling. If the threat doesn't see the cylinder lowering around him, and thus move, he will be captured. The likelihood of a threat just standing there is slim to none. The present invention addresses this issue with '827 by quickly capturing the suspect. The '827 does not explain how anesthetic gas will be filtered out of the cylinder so police and other employees won't fall victim to the anesthetic gas, unlike the present invention. '827 has many more motors, and other moving parts that make it work, which are not required with the present invention. Numerous parts equates to more maintenance, a problem which the present invention overcomes. '827 has no safety measures for law enforcement to extract the threat from the moveable compartment, unlike the present invention. '827 does not disclose enhanced bulletproof glass that will absorb a round from a high powered weapon nor is there a consideration for detecting bomb, unlike the present invention. The present invention also contains bomb detection as well as a x-ray lock down box.

U.S. Pat. No. 4,122,783 ("'783") to Pretini has a metal detector capability, and a moveable compartment that goes along an access path, to an access opening, in order for the person to enter a protected room. There is no provision in '783 for detecting bombs and there is no location inside the moveable compartment to separate the person from the weapon/bomb. '783 has no incapacitating gas. Entry to the compartment, in '783, can only receive one person at a time which does not allow for parent and child and/or disabled person with an adult who is assisting him. There are no safety measures for law enforcement to extract the threat from the moveable compartment in '783. There is no mention of enhanced bulletproof glass that will absorb a round from a high powered weapon in '783. The present invention also contains bomb detection as well as an x-ray lock down box.

U.S. Pat. No. 4,341,165 ("'165") to Calandritti is a cylinder control access with a weapons detector. In order for '165 to work, parts of the semicircle (going in opposite directions) enclosure have to move 90 degrees in order for the bulletproof glass to surround the threat. This is not disclosed in the present invention. '165 discloses a plurality of semicircles rotating about each other, unlike the present invention. '165 offers no protection to law enforcement because '165 just turns an armed gunman out of doors, and into the police hands without any disarming. '165 also discloses no capability for bomb detection, or enhanced bulletproof glass. '165 discloses no attempt to separation of threat and weapon. The present invention also contains bomb detection as well as an x-ray lock down box.

U.S. Pat. No. 4,586,441 ("'441") to Zekich utilizes a hand geometry reader and card reader capability, unlike the present invention. '441 does have a bomb detecting and conveyor capability. The present invention is anticipated for the use with public and therefore the hand geometry reader or card reader requirements of '441 could not work with the present invention. The canopy of '441 may not be bullet proof. Nor does it say that the bulletproof glass is enhanced or if it can stop a round from a high powered rifle. '441 does not allow for incapacitating gas. The present invention also contains bomb detection as well as an x-ray lock down box.

U.S. Pat. No. 4,461,221 ("'221") to Schandle applies to an exterior lobby doors of bank immediately locking once a holdup has been detected in the bank. When the robber leaves through the entry lobby door, it locks and he is caught in the lobby. The design of the '221 is restrictive in that in order for it to work, every bank will have to have a lobby. If there's no lobby, according to this design, there will be no catchment capability of the threat. There is no bomb detecting under the '221, unlike the present invention. Under '221, when the robber asks teller for money she gives his a target currency packet, which will have a remote device that will lock the exterior lobby door of the bank. Once the robber enters the lobby it will lock and he'll be caught. There's a metal detector in the lobby, and a box where he's supposed to deposit his gun. He's instructed to do so via intercom. So once he puts down the gun and surrenders, police will enter and arrest him. There is neither anything that will keep the robber from shooting up the bank before he leaves, nor is there anything to keep him from taking a hostage from the bank before entering the lobby. Also, there's no mention of bulletproof glass on the lobby enclosure. Also, while the robber is escaping, the tellers and other employees are supposed to tell the other customers not to leave the bank with him. This is a dangerous position to put civilian, tellers, and others. The present invention overcomes this issue. Again, in '221 there is no mention of bulletproof glass, unlike the present invention. There is neither a backup plan in case the suspect starts firing inside the lobby, nor is there anything about what to do if he doesn't put his weapon inside the weapon receptacle. The present invention also contains bomb detection as well as an x-ray lock down box.

U.S. Pat. No. 4,741,275 ("'275") to Lewiner is difficult to implement, and there is no mention of a metal detector or a bomb detector in the '275 patent. Bullet proof materials are not mentioned in '275. There is no mention of safely extracting a caught person from the security chamber in '275. The present invention also contains bomb detection as well as an x-ray lock down box.

U.S. Pat. No. 4,656,954 ("'954") to Tonali has a box shape, has one locked door from the exterior, one door opening to a room. '954 differs from the present invention in that it has a third door that opens into a 'discharge space' that is separate from the 'bank'. The notes of '954 also indicate that in the event of an alarm, it could cause considerable chaos in the flow of users. The present invention is designed to avoid just such a situation. '954 does disclose a metal detector and a security locker. '954 allows for only one user at a time. '954 does not mention bulletproof glass or bomb detection. The present invention also contains bomb detection as well as an x-ray lock down box.

U.S. Pat. No. 4,928,429 ("'429") to Colombo is a round catchment vestibule that is mounted in circular tracks. '429 has bulletproof material, in two of the panels which form 360 degrees. If no metal is detected, the panels separate and the person can exit. The person can exit, in '429, if panel 9 and 10 are driven along their respective runways, and conventional sensors means such as sensing platforms, photocells, and the like for operating said motive means. In other words, there are numerous of electronics that have to be in place and operating properly for this to work. '429 doses not have a manual override in case of emergency, as is found in the present invention. '429 does not mention bullet proof materials. The present invention also contains bomb detection as well as an x-ray lock down box.

U.S. Pat. No. 5,195,448 ("'448") to Sims teaches catchment capability states that is a 'safe' detention of robbers where he won't be hurt until police arrive, and police can easily extract robber. '448 states that its design does not need guards. The present invention has guards on location in case of emergency. '448 does capability to spray Nitrous Oxide to sedate a suspect, and also discloses the potential use of mace, tear gas, or other pacification materials. The present invention also contains bomb detection as well as an x-ray lock down box.

In '448 there is a sliding door that would cover the front entrance. There is neither a provision in '448 for bomb detection, nor enhanced bullet proof glass or material. '448 also appears to require a revolving door, unlike the present invention. The present invention also contains bomb detection as well as an x-ray lock down box.

U.S. Pat. No. 5,694,867 ("'867") to Diaz-Lopez teaches multiple security doors which lock to prevent more than one door from opening at a time, unlike the present invention. '867 discloses that the inner most door is prevented from opening when a weapon is detected by a metal detector. '867 uses a bullet proof chamber and access control unit. '867 uses an entrance and exit chambers, has 1$^{st}$ interlocking door for passage from a non-secure area into the entrance chamber and a second interlocking door for passage from the entrance to a secure area. '867 requires the entrance have a first floor mat and a second floor mat between the first and second doors to determine the location of the person in the entrance chamber. This is not required in the present invention. '867 does not disclose a bomb detector. The third door of '867 provides passage from a secure area into the exit chamber and a fourth interlocking door that gives passage to a nonsecure area. In '867 a third floor mat between the third and fourth door determines the location of the person within the exit chamber. '867 does not disclose incapacitating gas or bomb detection. The present invention also contains bomb detection as well as an x-ray lock down box and incapacitating gas.

U.S. Pat. No. 6,298,603 ("'603") to Diaz discloses bulletproof glass and building material along with a metal detector in access control chamber. In '603 the locks on the doors engage when metal is detected. In '603 the floor contact pad having a plurality of induction coils act as a metal detector for a weapon placed on the floor. This is unlike the present invention, which doesn't use floor pads. '603 has no bomb detection. '603 has no containment compartment for weapon or bomb and no incapacitating agents are disclosed in '603, unlike the present invention. The present invention also contains bomb detection as well as an x-ray lock down box.

US 2002/0154012 ("'012") to Risi discloses a first door or infeed at entrance of chamber, that goes through metal detector, and out of 2th door at exit. If no alarms sound in the operation of '012, then person is given access to protected area. According to '012, doors allow a person who went through metal detector and alarm sounded to pass back from the chamber into the infeed area and away from the protected area. '012 does not clearly explain if the person simply leave his items in the conveyor or not, and it is not clear if the suspect is ever out of the chamber as he goes back to the infeed area. According to '012, the enclosure is weighed after some cycles of cooperation to make sure no contraband is concealed inside chamber. In the present invention, there are no weights in the floor because of the clear design of the structure, all is visible. The present invention locks the doors and the person is captured. In the present invention, because the safety structure is constructed by clear glass, everyone and everything inside the structure is readily visible to the guards. '012 does not disclose a bomb detector. The structure of '012 defines the chamber to include one or more first doors movable between a closed position in which the first doors block the first opening and an open position in which the first doors do not block such opening. There are also one or more second doors movable between a closed position in which the second doors block the second opening and an open position in which the second doors do not block the second opening. The present invention also contains bomb detection as well as an x-ray lock down box.

US 2005/0237178 ("'178") to Stomski is a portable security portal that is mounted on a truck and responds to calls. '178 is bullet and bomb resistant. '178 has a balloon that opens from the top of the portal to catch the remnants of the bomb. '178 is not attached to a building, unlike the present invention. The design of this patent, '178 does not make it practical for the ongoing catchment need of businesses, schools, etc. unlike the present invention. The present invention also contains bomb detection as well as an x-ray lock down box.

US 2010/0147201 ("'201") to Mucio discloses a series of doors, locks, walls and signage present in a vestibule for the use in controlling access into a secured location. One distinction between '201 and the present invention is that a person in the safety enclosure of '201 could always leave the catchment room in case of emergency. In the present invention, the intent is to trap persons who are carrying weapons because it is undesirable to have an armed person loose in the community. The invention of '201 has no incapacitating agent to sedate the suspect and give police extra protection when extracting a suspect. The present invention also contains bomb detection as well as an x-ray lock down box and incapacity agents.

U.S. Pat. No. 6,724,304 ("'304") to Risi contains a metal detector and capture mechanism. The chamber of '304 is weighed, whereas there is no weighing in the present invention. There is no mention of bomb detection in the '304 patent. '304 lacks any sedation gas to be introduced, and no bomb blast protection unlike the present invention. The present invention also contains bomb detection as well as an x-ray lock down box.

U.S. Pat. No. 6,472,984 ("'984") to Risi has no bomb detection capability, unlike the present invention. '984 involves a catch and release policy. There is no sedation disclosed in the '984 patent. The present invention also contains bomb detection as well as an x-ray lock down box.

U.S. Pat. No. 6,745,520 ("'520") to Puskaric utilizes metal and explosives detectors, biometrics reader, physical recognition technology, electronic key lock, mechanical key lock, card reader, fingerprint reader, facial recognition technology, hand reader, vapor analyzer, spectrophotometric technique, and an iris scanner. The invention of '520 is made of bullet and explosive resistant material. '520 does not include a sedative. Unlike the present invention, the '520 doesn't have a weapon depositor, a lock down x-ray, or sedation gas. The present invention also contains bomb detection as well as an x-ray lock down box.

U.S. Pat. No. 8,269,600 ("'600") to Floyd has no weapons/bomb detection. There are no sedatives in '600. '600 directs a person who has weapon/bomb, will be directed to an area when a guard will conduct a physical search. There is no sedation in '600. There is no lockdown x-ray machine, nor weapons depository in '600. In '600, if the non-cleared person has passed a sensor the gate will be moved behind him to enable other cleared persons to pass through the gate while maintaining the channel created to the manual screening area. The present invention also contains bomb detection as well as an x-ray lock down box.

U.S. Pat. No. 6,348,866 ("'866") to Lopez focuses on the safety of the guard by building a guard stand several feet above the floor so the guard will have a good view of all the happenings on the floor. According to '866, pictures will show the guard in the bulletproof structure, an alarm, and the doors locking. According to '866 if there is a suspect w/gun inside a bank, the teller will push a button. This is readily distinguished from the present invention. The present invention also contains bomb detection as well as an x-ray lock down box.

U.S. Pat. No. 5,311,166 ("'166") to Frye does not have a metal/bomb detectors, sedation, lockdown of x-ray box, or weapon depository of the present invention. The present invention also contains bomb detection as well as an x-ray lock down box.

U.S. Pat. No. 5,983,578 ("'578") to Huttie in which the catchment is built off site, and transported to the location. If doors of '578 are breached, paths of shockwaves will occur through outer vestibule and the outer doors so that shock waves will not assault the inner door. According '578 the pressure created within the vestibule by a shock wave causes concrete at each end of the cylinder to fracture and propels 'flechette outward into an external area adjacent to the wall. This action would effectively incapacitate any suspect in the area. None of the aspects of the '578 are contemplated by the present invention. The present invention also contains bomb detection as well as an x-ray lock down box.

U.S. Pat. No. 7,053,785 ("'785") to Akins is a magnetometer and it detects the presence of metal, weapons, explosives, or other contraband in the object and alerts the person that the object may contain enough material to alarm the magnetometer. According to '785, people step on the machine to get a reading. In '785 there is no catchment capability, no bulletproof glass, and there is no provision for stopping and disabling an armed suspect from going back into the community and endangering the public. The present invention also contains bomb detection as well as an x-ray lock down box. The present invention also contains bomb detection as well as an x-ray lock down box.

U.S. Pat. No. 6,686,846 ("'846") to Lee is a decorative metal detector. There is no capture capability in '846. There is no lockdown or weapon depository in '846. '846 also has no bulletproofing of any kind. The present invention also contains bomb detection as well as an x-ray lock down box.

U.S. Pat. No. 6,359,582 ("'582") to MacAleese discloses a hand held machine to detect metal and nonmetal weapons in purses, briefcases, and under clothing and discerning weapons from belt buckles, coins, keys, phones, etc. The distance of operability in '582 is 4-15 yards. There is no containment in any manner disclosed in '582. The present invention also contains bomb detection as well as an x-ray lock down box.

U.S. Pat. No. 7,823,338 ("'338") to Slagel is an access control with card readers, one or more metal detectors, biometric readers, iris scanners, fingerprint readers facial recognition, explosive detectors, key locks, electronic key locks, electromagnetic (x-ray) and chemical detecting. In '338 the guard stays in control room while controlling the barrier device of the passing room. The control room has a detecting system for scanning belongings of individuals passing through the passing room. There is a conveyor, but no lock down capacity, unlike the present invention. '338 is designed for identifying persons and weapons rather than containment of same, as does the present invention. '338 makes no mention about bullet resistant materials. The present invention also contains bomb detection as well as an x-ray lock down box.

US 2014/0115965 ("'965") to Raynal discloses an obstacle that crosses a passageway for the entry/exit to/from restricted area. '965 does not teach or suggest anything about weapon and/or bomb detection. '965 does not mention the use of bullet resistant materials used in construction. The present invention also contains bomb detection as well as a x-ray lock down box.

U.S. Pat. No. 6,484,650 ("'650") to Stomski discloses bullet proof chambers for passage of persons and locking of specific person in a queue. '650 discloses a conveyor to inspect hand held items, manual and automatic controls for detaining person. '650 addresses several queues for airline passengers. '650 offers no real protection for a bomb/weapon for those innocent persons/guards who are being processed in adjacent queues. The present invention offers protection for bystanders. The present invention also contains bomb detection as well as an x-ray lock down box.

SUMMARY

In several embodiments of the present invention, the present invention operates under several parameters.

It is impossible to pinpoint the next public and fatal shooting, but we can seek to protect our work, educational, recreational etc. facilities by stopping the 'threat' before an assailant, and his/her weapons enters into the populated section of a building.

In several embodiments of the present invention, the present invention can provide a humane capture and detainment capability for an armed 'threat' by creating a substantially bulletproof (walls, floor, ceiling, doors, baffles, and metal frames and hardware) structure that is attached to the front door or restricted walkway through which people must travel.

In several embodiments of the present invention, the present invention could provide signage and verbal instruction in English and Spanish (other languages when appropriate) by entrance to building on how to use the invention. Along with this, in some embodiments of the present invention there could be an advanced notices via ads on Internet, TV, etc. explaining the safety features of the invention. In several embodiments of the present invention the entire encapsulating structure is built of clear bomb resistant materials.

In many embodiments of the present invention when a person opens the exterior door of the business, or enters into a walkway, they can open the entrance door to the inventive device. Once a person steps through door threshold, it will close and lock behind him. In several embodiments of the present invention when a person walks through the door they are essentially detained and during this time they need to be scanned by a metal detector and a Gas Ionization Explosive Detector ("GIED"). If there is no alarm on either of those instruments, the exit door unlocks, and the person leaves the catchment chamber. The exit door will close and relock behind the person exiting.

In some embodiments of the present invention, before a person passes through the metal detector they will put their belongings on a tray to his their side. A conveyor belt can then carry the belongings through an x-ray machine. If metal is detected, the x-ray compartment will automatically lock, and the metal will be seized. At this time the person will no longer have control of the metal object.

In some embodiments of the present invention, after placing items on conveyor, the person will walk forward through the metal detector. In this embodiment of the present invention if the person refuses to walk forward, it does not matter, because they are still captured in the containment area and unable to exit the security structure itself.

In several embodiments of the present invention, to the side of the metal detector will be a GIED which is designed to detect particular elements needed in the manufacture of bombs. If the GIED detects any bomb material, an alarm will sound. In some embodiments of the present invention the x-ray machine will be specifically retooled so as to provide a containment box made of bomb blast resistant materials, which will minimize any blast activity from negatively impacting the restricted area, and any persons therein. In some embodiments of the present invention the GIED can be mounted on the wall.

In some embodiments of the present invention if the person, the weapon and/or bomb remains captured, and a guard (who can be local or remote) can immediately notify police, and begin the evacuation of the building. When either metal and/or the GIED are activated, an alarm sounds, the captured person will be notified by security personnel via public address system in the invention that he/she is being held for law enforcement, and that he should, if he already has not, abandon his weapons (those that are not being held by the x-ray capture) by putting them into a weapon depository and surrender to police. In many embodiments of the present invention the weapon depository is constructed of heavy duty blast resistant material to help protect the facility in the case of a bomb blast.

In some instances if the person does not comply, a sedation compound, which will incapacitate him will be introduced. In this embodiment of the present invention, once the person has been incapacitated, and police are present at the scene, the sedation material will cease, and it will slowly be syphoned out of the catchment chamber. In this way, law enforcement will have enough time to enter the catchment chamber to restrain the sedated person so he will not be able to hurt himself or anyone else. However, if a bomb is involved in this catchment, police will have to follow their protocol on how to extract the suspect, secure him, then attend to the bomb.

In most instances if the person is not armed, and no weapon, including a bomb is detected, they will simply follow the proffered instructions and walk out of the metal detector, and go through the exit door into the building or hallway.

In many embodiments of the present invention video cameras could be installed in areas of the structure. In many embodiments of the present invention, the hard edges of the structure could have padding installed because if incapacitating sedation material is administered, the person might fall.

In several embodiments of the present invention, the present invention is a non-threatening structure to personnel or even children because it appears as a large clear glass box sitting in aluminum frames. The glass could be painted or decals applied to make the invention more aesthetically appealing.

In several embodiments the present invention can offer one, or many advantages. The 'threat' cannot enter a facility through any other door besides the entry door to the present invention. All employees must also enter through the present invention. If metal is detected the 'threat' and the weapon are locked inside the present invention and, an alarm is activated. If a threat tries to shoot while inside the invention the discharged bullet will be absorbed and embedded inside the bomb blast resistant walls, floors or ceilings. In some embodiments, when the bomb blast resistant wall materials are impacted by a high powered round, it will shatter, but remain in place. The wall material will not collapse. In some embodiments, air flow would be provided by bulletproof baffle grills which are installed above each door. The present invention is benign in its appearance because it is only a thick, clear glass box sitting in metal frames. A sedative form of air borne sedation material could be introduced into the present invention to sedate the 'threat' so as to make capture by police even more safe.

In some embodiments of the present invention, the invention is a safety enclosure system comprising: a walled enclosure with impact resistant walls, an entrance door and exit door, said walled enclosure further comprising; an inner scanning chamber and inner storage chamber with said storage chamber located interior to the inner scanning chamber, said inner scanning chamber wherein said entrance door and said exit door are located on opposite ends of say inner scanning chamber, said inner scanning chamber further comprising an x-ray metal detector with a conveyor belt, a walkthrough metal detector, a gas ionization explosives detector, and a weapons depository unit located in the interior of the inner scanning chamber, said x-ray metal detector having material capture capability said inner storage chamber further comprising an air conditioning unit and a sedation dispenser containing sedation material; said inner storage chamber further comprising and enclosure with ports to access the inner scanning chamber by which said sedation dispenser can pump sedation material from the storage chamber into said inner scanning chamber, said entrance door and said exit door further comprising baffles above said entrance door and said exit door for the removal of sedation material; wherein said metal detector is positioned in said inner scanning chamber such that a user would need to walk through said metal detector to go from the entrance door to the exit door, wherein said entrance and exit doors are locked when said user enters into the inner scanning chamber, and wherein a user maybe be confronted with said sedation material when released into said inner scanning chamber. In some embodiments of the present invention the system further comprises: a user may place an object to be scanned on said conveyor belt to be run through said x-ray metal detection machine; furthermore, if said object is a weapon or a bomb it is captured in said x-ray machine. In some embodiments of the present invention the system further comprises: if a weapon is detected by one or more of the following, in combination or individually: said x-ray detector, said metal detector, or said gas ionization explosives detector, said sedation material is released in to the inner scanning chamber therein rendering a user incapacitated. In some embodiments of the present invention the system further comprises: if a bomb is detected by one or more of the following, in combination or individually: said x-ray detector, said metal detector, or said gas ionization explosives detector, said sedation material is released in to the inner scanning chamber. In some embodiments of the present invention the system further comprises: if a gun is detected by one or more of the following, in combination or individually: said x-ray detector, said metal detector, or said gas ionization explosives detector, said sedation material is released in to the inner scanning chamber. In some embodiments of the present invention the system further comprises: said walled enclosure with a frame further comprises closing baffles located above said entrance and said exit doors to allow air in or to prevent gas from escaping said enclosure. In some embodiments of the present invention the system further comprises: said walled enclosure with a frame further comprises a ceiling attached to said walled enclosure with a frame. In some embodiments of the present invention the system further comprises: said ceiling has a first exhaust fan attached near said exit door and a second exhaust fan located near said entrance door, a upper tube and a lower tube connected to said sedation materials container; and wherein said first and second exhaust fans can pump sedation materials through said upper tube, through said lower tube and into said sedation materials container.

In some embodiments the present invention, is a method for using a safety enclosure system comprising; obtaining a safety enclosure system; said safety enclosure system further comprising; a walled enclosure with impact resistant walls, an entrance door and exit door, said walled enclosure further comprising; an inner scanning chamber and inner storage chamber with said storage chamber located interior to the inner scanning chamber, said inner scanning chamber wherein said entrance door and said exit door are located on opposite ends of say inner scanning chamber; said inner scanning chamber further comprising an x-ray metal detector with a conveyor belt, a walkthrough metal detector, a gas ionization explosives detector, and a weapons depository unit located in the interior of the inner scanning chamber; said x-ray metal detector having material capture capability said inner storage chamber further comprising an air conditioning unit and a sedation dispenser containing sedation material; said inner storage chamber further comprising and enclosure with ports to access the inner scanning chamber by which said sedation dispenser can pump sedation material from the storage chamber into said inner scanning chamber; said entrance door and said exit door further comprising baffles above said entrance door and said exit door for the removal of sedation material; wherein said metal detector is positioned in said inner scanning chamber such that a user would need to walk through said metal detector to go from the entrance door to the exit door; having a user enter said entering into said safety enclosure; wherein said entrance and exit doors are locked when said user enters into the inner scanning chamber; having said user pass through said metal detector scan; having said user scanned by said gas ionization explosives detector; wherein a user maybe be confronted with said sedation material when released into said inner scanning chamber if said user fails said metal detector scan; and wherein a user maybe be confronted with said sedation material when released into said inner scanning chamber if said user fails said gas ionization explosive detector, having user that is not confronted with sedation materials leave the safety enclosure through the exit door. In some embodiments of the present invention the method further comprises the step of; placing an object to be scanned on said conveyor belt to be run through said x-ray metal detection machine; furthermore, if said object is a weapon or a bomb it is captured in said x-ray machine. In some embodiments of the present invention the method further comprises the step of; detecting a weapon by one or more of the following, in combination or individually: said x-ray detector, said metal detector, or said gas ionization explosives detector, releasing said sedation material into the inner scanning chamber therein rendering a user incapacitated. In some embodiments of the present invention the method further comprises the step of, detecting a bomb by one or more of the following, in combination or individually: said x-ray detector, said metal detector, or said gas ionization explosives detector, releasing said sedation material into the inner scanning chamber therein rendering a user incapacitated. In some embodiments of the present invention the method further comprises the step of; detecting a gun by one or more of the following, in combination or individually: said x-ray detector, said metal detector, or said gas ionization explosives detector, releasing said sedation material into the inner scanning chamber therein rendering a user incapacitated. In some embodiments of the present invention the method further comprises the step of including on said walled enclosure with a frame further closing baffles located above said entrance and said exit doors to allow air in or to prevent gas from escaping said enclosure. In some embodiments of the present invention the method further comprises the step of, attaching to said walled enclosure with a frame and a ceiling attached to said walled enclosure with a frame. In some embodiments of the present invention the method further comprises the step of, attaching to said ceiling a first exhaust fan attached near said exit door and a second exhaust fan located near said entrance door, a upper tube and a lower tube connected to said sedation materials container; and pumping sedation materials through said first and second exhaust fans through said upper tube, through said lower tube and into said sedation materials container.

In some embodiments the present invention is a security scanning enclosure comprising: a walled enclosure with a frame with impact resistant walls, an entrance door and exit door, said walled enclosure with a frame further comprising; remote cameras capable of transmitting video feed attached to the interior of said walled enclosure with a frame; an inner scanning chamber and inner storage chamber with said storage chamber located interior to the inner scanning chamber; said inner scanning chamber wherein said entrance door and said exit door are located on opposite ends of say inner scanning chamber, said inner scanning chamber further comprising an x-ray metal detector with a conveyor belt, a walkthrough metal detector, a gas ionization explosives detector, and a weapons depository unit located in the interior of the inner scanning chamber, said x-ray metal detector having material capture capability; said inner storage chamber further comprising an air conditioning unit and a sedation dispenser containing sedation material; said inner storage chamber further comprising and enclosure with ports to access the inner scanning chamber by which said sedation dispenser can pump sedation material from the storage chamber into said inner scanning chamber; said entrance door and said exit door further comprising baffles above said entrance door and said exit door for the removal of sedation material; wherein said metal detector is positioned in said inner scanning chamber such that a user would need to walk through said metal detector to go from the entrance door to the exit door; wherein said entrance and exit doors are locked when said user enters into the inner scanning chamber, and wherein a user maybe be confronted with said sedation material when released into said inner scanning chamber. In some embodiments of the present invention the present invention further comprises: a user may place an object to be scanned on said conveyor belt to be run through said x-ray metal detection machine; furthermore, if said object is a weapon or a bomb it is captured in said x-ray machine. In some embodiments of the present invention the present invention further comprises: if a weapon is detected by one or more of the following, in combination or individually: said x-ray detector, said metal detector, or said gas ionization explosives detector; said sedation material is released in to the inner scanning chamber therein rendering a user incapacitated. In some embodiments of the present invention the present invention further comprises: if a bomb is detected by one or more of the following, in combination or individually: said x-ray detector, said metal detector, or said gas ionization explosives detector, said sedation material is released in to the inner scanning chamber. In some embodiments of the present invention the present invention further comprises: if a gun is detected by one or more of the following, in combination or individually: said x-ray detector, said metal detector, or said gas ionization explosives detector, said sedation material is released in to the inner scanning chamber. In some embodiments of the present invention the present invention further comprises: said walled enclosure with a frame further comprises closing baffles located above said entrance and said exit doors to allow air in or to prevent gas from escaping said enclosure; said walled enclosure with a frame further comprises a ceiling attached to said walled enclosure with a frame. In some embodiments of the present invention the present invention further comprises: said ceiling has a first exhaust fan attached near said exit door and a second exhaust fan located near said entrance door, a upper tube and a lower tube connected to said sedation materials container, and wherein said first and second exhaust fans can pump sedation materials through said upper tube, through said lower tube and into said sedation materials container.

BRIEF DESCRIPTION OF THE DRAWINGS

For a more complete understanding of the present disclosure, and the advantages thereof, reference is now made to the following descriptions to be taken in conjunction with the accompanying drawings describing specific embodiments of the disclosure, wherein.

DETAILED DESCRIPTION

In the following description, certain details are set forth such as specific quantities, sizes, etc. . . . so as to provide a thorough understanding of the present embodiments disclosed herein. However, it will be evident to those of ordinary skill in the art that the present disclosure may be practiced without such specific details. In many cases, details concerning such considerations and the like have been omitted inasmuch as such details are not necessary to obtain a complete understanding of the present disclosure and are within the skills of persons of ordinary skill in the relevant art.

Referring to the drawings in general, it will be understood that the illustrations are for the purpose of describing particular embodiments of the disclosure and are not intended to be limiting thereto. Drawings are not necessarily to scale.

One, or more, illustrative embodiments incorporating the invention disclosed herein are presented below. Applicants have created a revolutionary and novel system and method of an improved security, monitoring and safety system with containment and method of use.

While most of the terms used herein will be recognizable to those of ordinary skill in the art, it should be understood, however, that when not explicitly defined, terms should be interpreted as adopting a meaning presently accepted by those of ordinary skill in the art. In cases where the construction of a term would render it meaningless or essentially meaningless, the definition should be taken from Webster's Dictionary, 11th Edition, 2008. Definitions and/or interpretations should not be incorporated from other patent applications, patents, or publications, related or not, unless specifically stated in this specification or if the incorporation is necessary for maintaining validity. "Safety structure", "safety system", "security scanning enclosure" or "safety enclosure system" can be used interchangeably and are defined herein as any structure designed to hold a threat. "Bulletproof" or "bullet resistant" as defined herein as any material designed to capture or impede a live round from a high powered (or less) rifle or handgun without complete structural failure. "Humane capture" as described herein means any capability to hold a threat without inflicting pain nor causing harm or killing the threat "Bomb resistant material" as defined herein is any material that not only is resistant to a bomb blast, but is a blast-resistant material that is strong enough to withstand the force of an explosion. "Metal Detector" as defined herein as any machine capable of detecting metal, it also includes any fill body scanners which are capable to electronically detect any suspicious items that can be seen through a person's clothing and which are secured to a human body. "Weapon depository" as defined herein as any enclosure comprised of bomb resistant material with a bomb resistant locking lid in which to place a bomb and/or weapon. "Gas Ionization Detector" system as defined herein is any device that is capable of detecting and identifying any minute airborne materials that are required to manufacture bombs. "Incapacitated" as defined herein is unable to use arms or legs in a functional manner.

Although several preferred embodiments of the present invention have been described in detail herein, the invention is not limited hereto. It will be appreciated by those having ordinary skill in the art that various modifications can be made without materially departing from the novel and advantageous teachings of the invention. Accordingly, the embodiments disclosed herein are by way of example. It is to be understood that the scope of the invention is not to be limited thereby.

Figure 1:
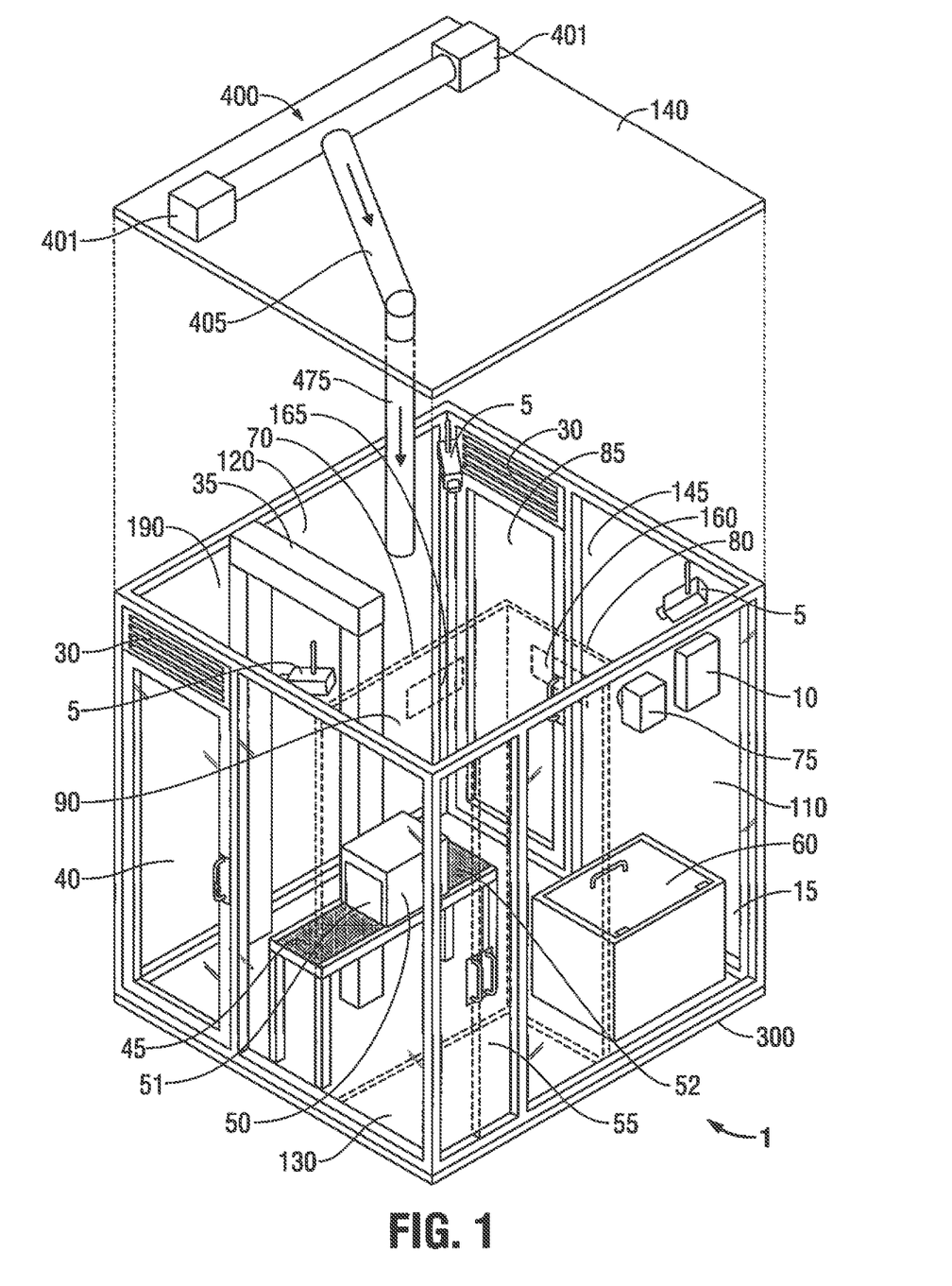
FIG. 1 illustrates one embodiment of the present invention partially exploded view.

FIG. 1 illustrates one embodiment of the present invention in partially exploded view. As shown the improved security, monitoring and safety system with containment or safety system 1, can be comprised of two main sections, the ceiling 140 and the containment frame with walls 300.

It is preferable that in construction the ceiling 140 and the frame with walls 300 are bomb and/or bullet resistant. In many embodiments of the present invention the ceiling 140 and walls 110 maybe transparent, solid, or decorated. In many embodiments the ceiling 140 and walls 110 maybe constructed of shock resistant materials. In many embodiments there may be a floor 130 attached to the lower portion of the frame with walls 300 in a manner known in the art. By way of example, in some embodiments the floor 130 can be made of bomb resistant cement and fitted with resistant framing. In many embodiments of the present invention the floor 130 is made of shock, bullet, or bomb resistant materials. In several embodiments of the present invention the ceiling 140 attaches to the lower portion of the frame with walls 300 in a manner known in the art. The attachments between the ceiling 140 and lower portion of the frame with walls 300 are preferably done in a manner to ensure that there is an air tight seal between. FIG. 1 also illustrates a walls 15 and 120 which are exemplar walls in the present invention. In many embodiments of the present invention, the walls 15 and 120 are constructed of bomb, bullet and/or impact resistant materials. In several embodiments of the present invention, the walls 15 and 120 maybe transparent.

Figure 10:
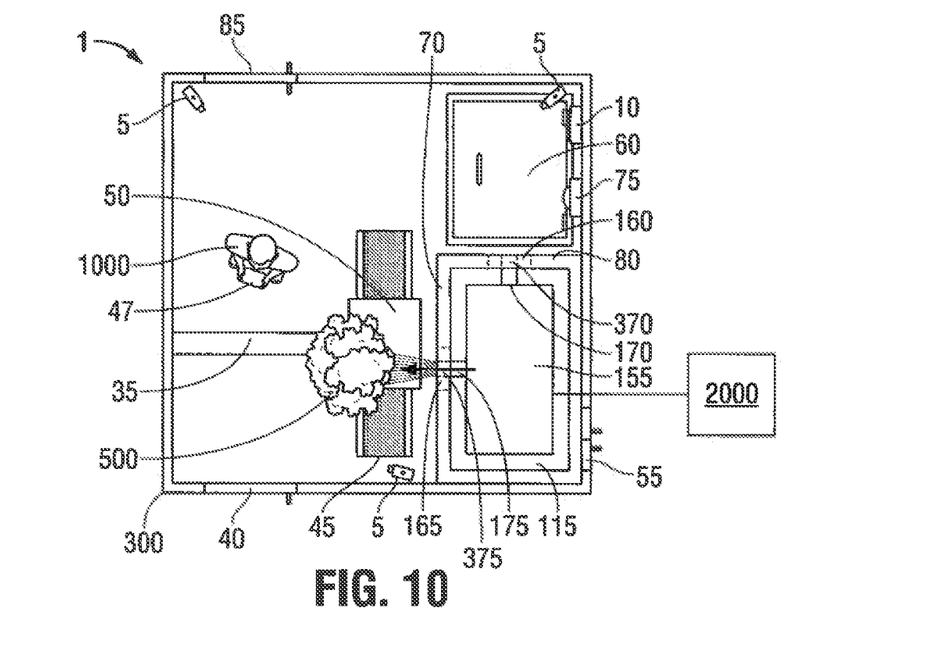
FIG. 10 illustrates one embodiment of the present invention in an assembled view with a user having passed through the metal detector and sedation material entering the inner scanning chamber.
Figure 11:
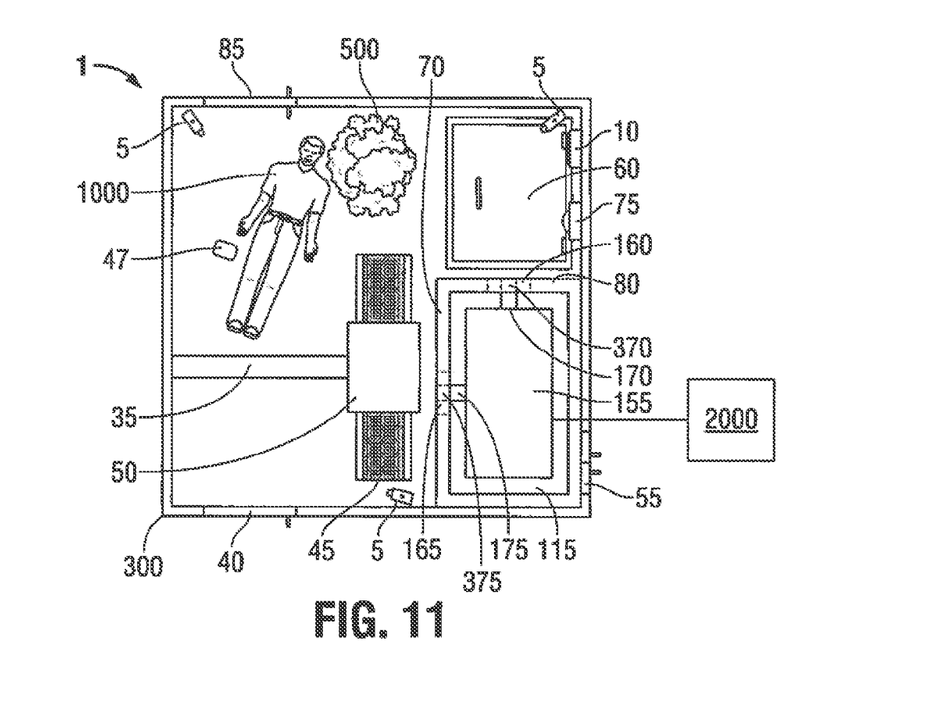
FIG. 11 illustrates one embodiment of the present invention in an assembled view with a user having been knocked out by sedation material in the inner scanning chamber.

As illustrated in FIG. 1, in several embodiments of the present invention, the ceiling 140 has a ventilation system 400 attached to the top of the ceiling 140. As shown the ventilation system 400 is designed to have the sedation material tubing 405, or upper tube and exhausts fan 401 to syphon the air from the safety structure 1 so that nothing gets through to the air in the remainder of the facility, school, etc. outside of the safety structure 1. The exhaust fans 401 can be those as known in the art and may contain HEPA filters and the like to promote the syphoning of any sedation material 500 that is introduced in the safety structure system 1. In some embodiments the HEPA filter will retain all sedation gas 500 materials (FIGS. 10 and 11). In many embodiments of the present invention the exhaust fans 401 are located near the baffles 30. In many embodiments of the present invention the baffles 30 can be operated from the exterior of the present invention by an exterior operator so that a user 1000 (FIG. 2) would not suffocate with closed baffle 30. Also illustrated is the pipe 475 (which is optional), known also as lower pipe or lower tube, and can conduct the sedation gas 500 backing into the sedation dispenser 155 for reuse.

As illustrated in FIG. 1, in several embodiments of the present invention, the interior of the safety system 1 is constructed to have two interior chambers, the inner scanning chamber 190 and the storage chamber 90. In many embodiments of the present invention the scanning chamber 190 and the storage chamber 90 are separated by two bomb, impact or bullet resistant walls 70 and 80. The resistant walls 70 and 80 run the height of the frame with walls 300 and attach, preferably, to the ceiling 140 when the safety structure system 1 is assembled. As shown, the resistant walls 70 and 80 have two ports 165 and 160 respectfully, by which sedation material 500 can be pumped from the storage chamber 90 into the scanning chamber 190 (See FIGS. 10-11). As illustrated chamber 90 has a set of bomb, impact or bullet resistant doors 55 which can be opened to allow an operator 2000 to put materials and equipment into the storage chamber (See FIGS. 2-11).

As illustrated in FIG. 1, in several embodiments of the present invention, the inner scanning chamber 190 has an entrance door 40 and an exit door 85. Both the doors 40 and 85 are preferably composed of bomb, impact or bullet resistant materials. Located above each door 40 and 85 are baffles 30 which are again preferably composed of bomb, impact or bullet resistant. During various operations the baffles 30 can be opened to allow for air to circulate though the safety system 1, or may be closed to prevent sedation material 500 from escaping the safety system 1. In many embodiments of the present invention the baffles 30 are located near the exhaust fans 401.

In several embodiments of the present invention when a user enters the safety system 1 the doors 40 and 85 automatically lock. (See FIGS. 2-11). In many embodiments of the present invention, the baffles 30 are made of bomb, impact or bullet resistant materials.

As illustrated in FIG. 1, in several embodiments of the present invention, the inner scanning chamber 190 has a metal detector 35 as is known in the art for detecting metals and/or performing body scans. As illustrated the metal detector 35 substantially forms a gateway through which a user must pass if they which to proceed through the safety system. In several embodiments of the present invention the metal detector 35 will be flush with the bomb, bullet or impact resistant wall 130 of the frame with walls 300. The metal detector 35 can run the height of the wall 130 in some embodiments of the present invention as well. As shown the metal detector 35 may contact the conveyor belt system 45 of the present invention as well. In some embodiments of the present invention the entrance door 40 will be flush with the frame with walls 300. In some embodiments of the present invention, the conveyor 45 will be flush with wall 70, in that way, the user 1000 is unable to push anything between the edge of the conveyor 45 and the wall 70.

As illustrated in FIG. 1, next to the metal detector 35 is a conveyor belt 45 that runs through a detection machine 50. The detection machine 50 is one known in the art and maybe capable of detecting metals, ceramic weapons, contraband, plastic explosives, trace elements of metal weapons/bombs. In some embodiments of the present invention the detection machine 50 will also be able to differentiate shapes of items, such as the outline of a non-metal handgun and other materials. In many embodiments of the present invention the detection machine 50 has the capacity to contain materials that are suspect by closing the doors 51 and 52 respectfully, therein preventing a user from accessing said materials.

As illustrated in FIG. 1, located behind the metal detector 35 is a weapons depository 60. In several embodiments of the present invention this could be located in front of the metal detector 35 as well. The weapons depository 60 is designed to have a user place the weapon that is detected by the metal detector 35 off of their person and on the depository 60 so that the used can no longer access the weapon. In many embodiments of the present invention the weapon depository 60 can be constructed of bomb resistant material which can offer another layer of protection from a bomb blast. Further illustrated is the Gas Ionization Emissions Detector ("GIED") 75. The GIED 75 is preferably of a type known in the art for detection of particles usually associated with bomb construction materials. The GIED 75 can be located in multiple locations in the inner scanning chamber 190. Also illustrated is the public announcement system ("PA System") 10. The PA system 10 is preferably one known in the art for providing oral instructions. In operation the PA system 10 can provide instruction for a user located in safety system 1. As illustrated in FIG. 1, located in various areas of the inner scanning chamber 190 are video cameras 5 as are known and used throughout the industry. As illustrated is wall 15 which is preferable made of shock, bullet, or bomb resistant materials and have attached to it PA system 10 and GIED 75. In some embodiments of the present invention an operator 2000 can address a user 1000 located inside the present invention and provide specific instructions and direction to the user 1000. If user does not follow spoken demands, the operator 2000 can activate the sedation dispenser 155 (FIG. 2).

Figure 2:
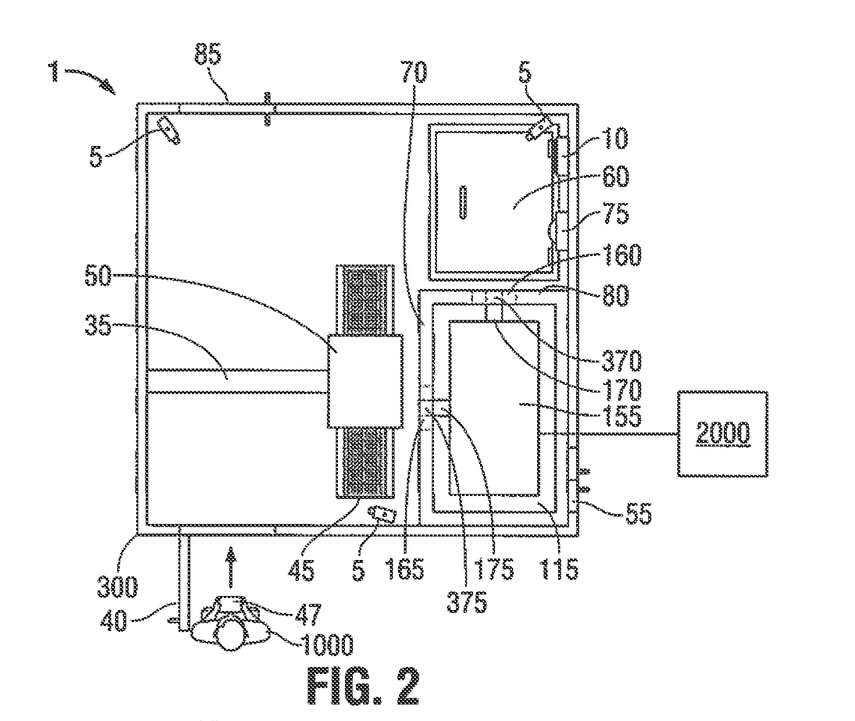
FIG. 2 illustrates one embodiment of the present invention in an assembled view with a user entering into the invention.

FIG. 2 illustrates one embodiment of the present invention in an assembled view with a user entering into the invention. As shown in FIG. 2 a user 1000 enters the safety system 1 via opening door 40. Illustrated also is the air conditioner unit 115. The air conditioner unit 115 is of the type usually used in the industry that would be capable of providing air to the inner scanning chamber 190. Air can enter the inner scanning chamber through pipes 370 and 375 and then through portals 160 and 165. Also illustrated on top of the air conditioner unit 115 is the sedation dispenser 155. The sedation dispenser 155 is preferably designed to contain sedation material or compounds that can render a human incapacitated when inhaled, this is generically referred to as the sedation material 500. In certain time of operation the sedation material 500 moves through pipes 175 and 170 and through the portals 165 and 160 respectfully so the sedation material 500 can enter into the inner scanning chamber 190 (FIG. 10). In certain applications the sedation material 500 can render the user 1000 incapacitated (FIG. 11). As shown in FIG. 2 the video cameras 5 can transmit a feed of the user entering in the safety system 1 and at all points prior to exiting the safety system. No sedation material 500 has been introduced into inner scanning chamber 190 at this point. As shown in FIGS. 2-11, the remote operator 2000 can obtain all data generated by the video cameras 5, metal detector 35, GIED 75, and/or detection machine 50 through standard information communications and as a result activate the sedation dispenser 155 or provide instructions via the PA system 10, as necessary. In several embodiments of the present invention, the remote operator 2000 can be located near the invention but not inside of the frame and walls 300.

Figure 3:
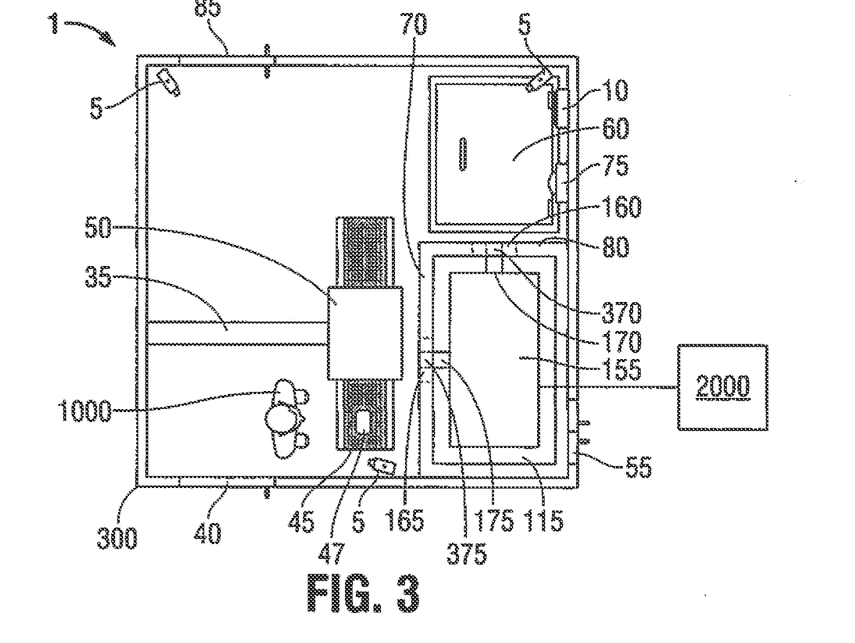
FIG. 3 illustrates one embodiment of the present invention in an assembled view with a user facing the conveyor belt.

FIG. 3 illustrates one embodiment of the present invention in an assembled view with a user 1000 moving to place an object 47 on the conveyor belt 45. In many embodiments of the present invention, the doors 40 and 85 are locked after a user 1000 enters into the safety system 1. After being placed the object 47 will move on the conveyor belt through the detection machine 50 and be scanned. If there is anything that is a weapon or bomb the detection machine 50 can close its doors 51 and 52 and entrap the object 47. In this instance a remote operator 2000 could activate the sedation material 500 to be released into the inner scanning chamber 190 therein rendering the user 1000 incapacitated FIG. 11.

Figure 4:
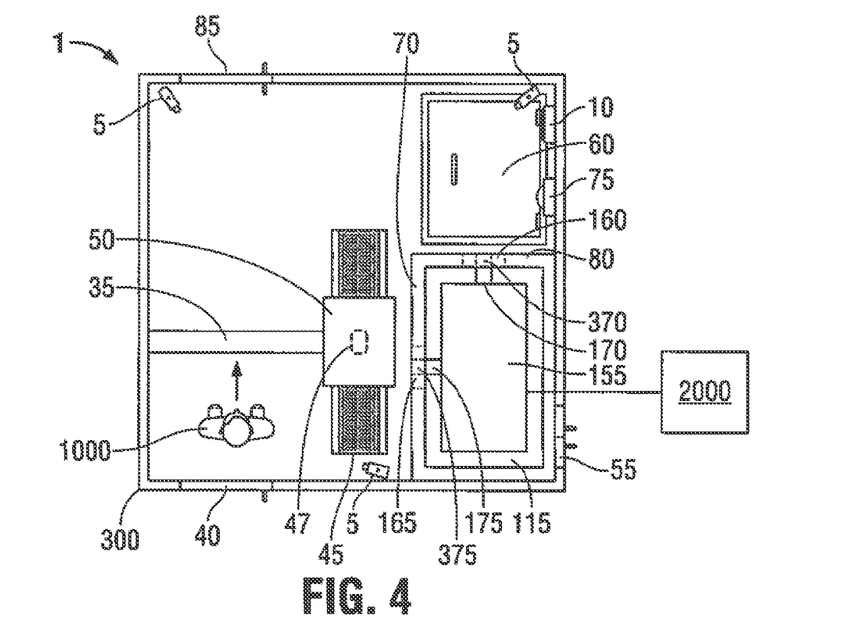
FIG. 4 illustrates one embodiment of the present invention in an assembled view with a user facing the metal detector.
Figure 5:
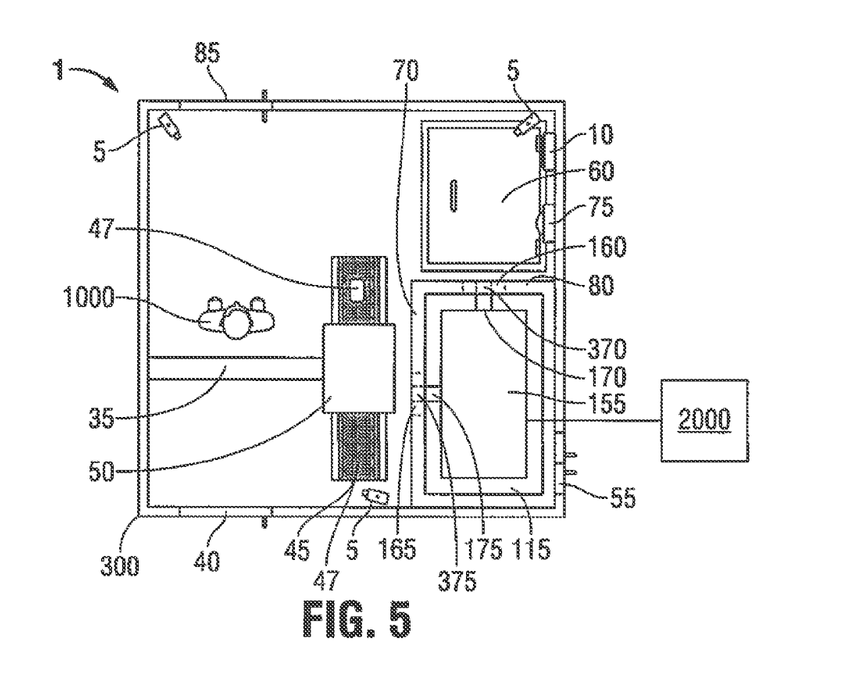
FIG. 5 illustrates one embodiment of the present invention in an assembled view with a user having passed through the metal detector.

FIGS. 4 & 5 illustrate one embodiment of the present invention in an assembled view with a user 1000 moving through the metal detector 35. It is important to note that in several embodiments of the present invention the user 1000 can walk straight through the metal detector 35 if they have no object 47. In other embodiments of the present invention the object 47 can be scanned before or after the user 1000 walks through the metal detector 35. If a weapon is discovered in the metal detector 35 a remote operator 2000 could activate the sedation material 500 to be released into the inner scanning chamber 190 therein rendering the user 1000 incapacitated FIG. 11.

Figure 6:
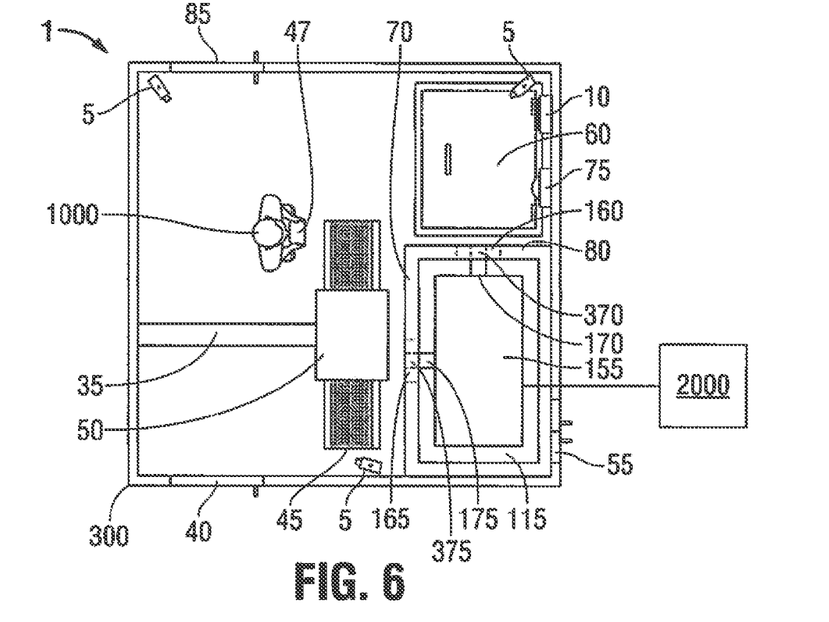
FIG. 6 illustrates one embodiment of the present invention in an assembled view with a user having passed through the metal detector and facing the conveyor belt.
Figure 7:
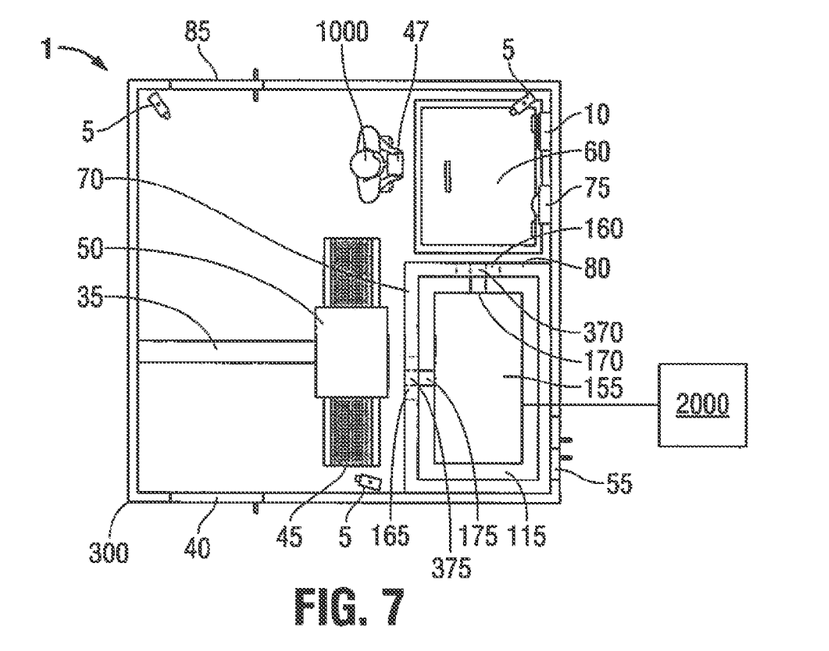
FIG. 7 illustrates one embodiment of the present invention in an assembled view with a user having passed through the metal detector and facing the weapons depository and GIED.

FIGS. 6 & 7 illustrate one embodiment of the present invention in an assembled view with a user 1000 having moved through the metal detector 35 and retrieving the object 47. If the object 47 is a weapon or a weapon is detected on the user after going through the metal detector 35, then the user can place the object into the weapons depository 60. During this process the user is being additionally scanned by the GIED 75 for any bomb materials that may have gone unnoticed through the metal detector 35 or the detection machine 50. If a bomb is discovered by the GIED 75 a remote operator 2000 could activate the sedation material 500 to be released into the inner scanning chamber 190 therein rendering the user 1000 incapacitated FIG. 11.

Figure 8:
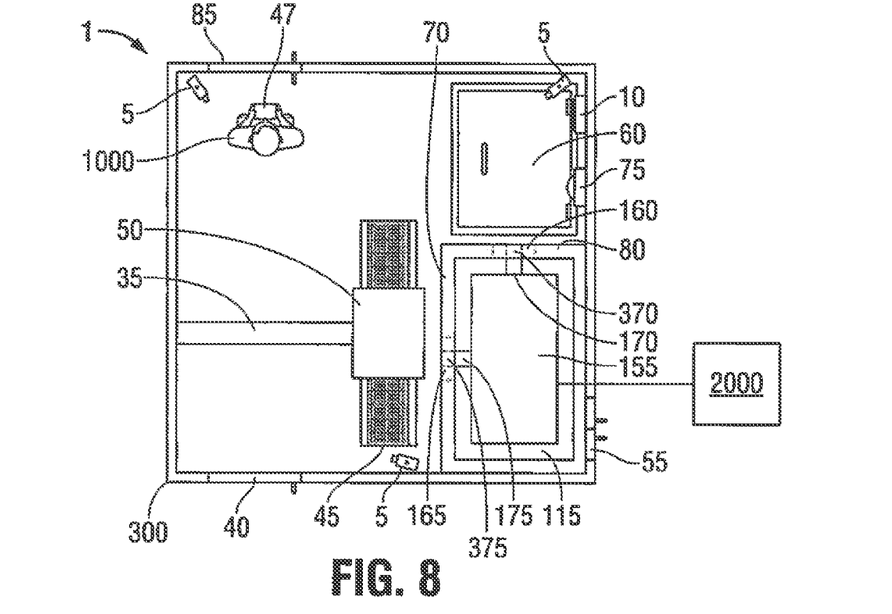
FIG. 8 illustrates one embodiment of the present invention in an assembled view with a user having passed through the metal detector and facing the exit door.
Figure 9:
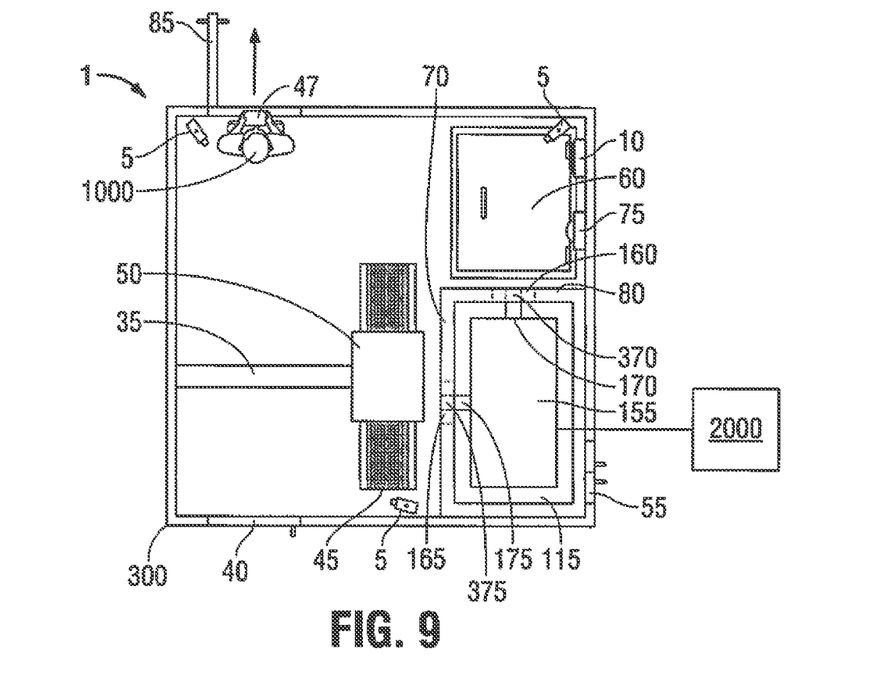
FIG. 9 illustrates one embodiment of the present invention in an assembled view with a user having passed through the metal detector and exiting the inventive device.

FIG. 8 illustrates a user 1000 facing the exit door 85 after being scanned by the metal detector 35 and the GIED 75 as well as having picked up the object 47 cleared through the scanner and the GIED 75. Once cleared the exit door 85 is unlocked and opened for the user 1000 to leave the safety device 1 (FIG. 9). In several embodiments of the present invention, at all times in the safety device 1 the user is viewed through the cameras 5 located in the safety device 1. In many embodiments of the present invention in the safety device a PA system 10 is also present in the inner scanning chamber 190 to instruct the user 1000 on what they are to do in order to proceed through the safety device 1, or in the case of a threat how the user 1000 is to proceed in disarming themselves.

FIG. 10 illustrates a user 1000 with an object 47 that is harmful to others such as a weapon, bomb or biological agent. In this scenario, the baffles 30 (FIG. 1) are shut preventing any air or contaminants from escaping the safety device by a signal from remote operator 2000. Instructions are promptly given through the PA 10 for the user 1000 to place the object 47, and any other harmful items, in to the weapons disposal unit 60. If the user 1000 is compliant law enforcement can then detain the user 1000 after an all clear signal is given and the exit door 85 is opened. If the user is not complaint then sedation material 500 will be released from the sedation dispenser 155 through the tubes 375 and 370 through the portals 165 and 170 and into the inner scanning chamber 190.

In some embodiments, without a HEPA filter in the exhaust fan 401, once inhaled (FIG. 11) the user 1000 is rendered incapacitated and the threat is neutralized. After the user is rendered incapacitated the exhaust fans 401 will pump the sedation material 500 from the inner chamber 190 and through the tube 405 back into the sedation dispenser 155 via tube 475. Simultaneously, fresh air will be pumped into the inner chamber 190 through the air conditioner 115. Once the sedation material 500 has been removed, the baffles 30 will open allowing further circulation of air. Once the baffles 30 are opened and the user 1000 is still incapacitated then the exit door 85 is opened and law enforcement can enter the safety system 1 to remove the user 1000 and any necessary objects 47.

In some embodiments, with a HEPA filter in the exhaust fan 401, once inhaled (FIG. 11) the user 1000 is rendered incapacitated and the threat is neutralized. After the user is rendered incapacitated the exhaust fans 401 will pump the sedation material 500 from the inner chamber 190 into the HEPA filter. Simultaneously, fresh air will be pumped into the inner chamber 190 through the air conditioner 115. Once the sedation material 500 has been removed, the baffles 30 will open allowing further circulation of air. Once the baffles 30 are opened and the user 1000 is still incapacitated then the exit door 85 is opened and law enforcement can enter the safety system 1 to remove the user 1000 and any necessary objects 47.

In the case in which the user 1000 detonates a bomb or fires a weapon, it is envisioned that the frame and walls 300 be composed of bomb, bullet or impact resistant materials as known in the art. In the case of fire arms being discharged a remote operator 2000 could activate the sedation material 500 to be released into the inner scanning chamber 190 therein rendering the user 1000 incapacitated FIG. 11.

Although several preferred embodiments of the present invention have been described in detail herein, the invention is not limited hereto. It will be appreciated by those having ordinary skill in the art that various modifications can be made without materially departing from the novel and advantageous teachings of the invention. Accordingly, the embodiments disclosed herein are by way of example. It is to be understood that the scope of the invention is not to be limited thereby.

I claim:

1. A safety enclosure system comprising:
   a walled enclosure with a frame with impact resistant walls, an entrance door and exit door,
   said walled enclosure with a frame further comprising;
   an inner scanning chamber and storage chamber with said storage chamber located interior to the inner scanning chamber;
   said inner scanning chamber wherein said entrance door and said exit door are located on opposite ends of said inner scanning chamber,
   said inner scanning chamber further comprising an x-ray metal detector with a conveyor belt, a walkthrough metal detector, a gas ionization explosives detector, and a weapons depository unit located in the interior of the inner scanning chamber,
   said x-ray metal detector having material capture capability;
   said storage chamber further comprising an air conditioning unit and a sedation dispenser containing sedation material;
   said inner storage chamber further comprising an enclosure with ports to access the inner scanning chamber by which said sedation dispenser can pump sedation material from the storage chamber into said inner scanning chamber;
   said entrance door and said exit door further comprising baffles above said entrance door and said exit door for the removal of sedation material;
   wherein said metal detector is positioned in said inner scanning chamber such that a user would need to walk through said metal detector to go from the entrance door to the exit door;
   wherein said entrance and exit doors are locked when said user enters into the inner scanning chamber; and
   wherein a user maybe be confronted with said sedation material when released into said inner scanning chamber.

2. The system of claim 1 wherein;
   a user may place an object to be scanned on said conveyor belt to be run through said x-ray metal detection machine; furthermore,
   if said object is a weapon or a bomb said object is captured in said x-ray machine.

3. The system of claim 1 wherein;
   if a weapon is detected by one or more of the following, in combination or individually:
   said x-ray detector, said metal detector, or said gas ionization explosives detector,
   said sedation material is released in to the inner scanning chamber therein rendering a user incapacitated.

4. The system of claim 1 wherein;
   if a bomb is detected by one or more of the following, in combination or individually: said x-ray detector, said metal detector, or said gas ionization explosives detector;
   said sedation material is released in to the inner scanning chamber.

5. The system of claim 1 wherein;
   if a gun is detected by one or more of the following, in combination or individually: said x-ray detector, said metal detector, or said gas ionization explosives detector;
   said sedation material is released in to the inner scanning chamber.

6. The system of claim 1 wherein;
   said walled enclosure with a frame further comprises closing baffles located above said entrance and said exit doors to allow air in or to prevent gas from escaping said enclosure.

7. The system of claim 1 wherein;
   said walled enclosure with a frame further comprises a ceiling attached to said walled enclosure with a frame.

8. The system of claim 7 where in;
   said ceiling has a first exhaust fan attached near said exit door and a second exhaust fan located near said entrance door, a upper tube and a lower tube connected to said sedation materials container; and
   wherein said first and second exhaust fans can pump sedation materials through said upper tube, through said lower tube and into said sedation dispenser.

9. A method for using a safety enclosure system comprising;
   obtaining a safety enclosure system;
   said safety enclosure system further comprising;

a walled enclosure with impact resistant walls, an entrance door and exit door;

said walled enclosure further comprising;

an inner scanning chamber and inner storage chamber with said storage chamber located interior to the inner scanning chamber;

said inner scanning chamber wherein said entrance door and said exit door are located on opposite ends of said inner scanning chamber;

said inner scanning chamber further comprising an x-ray metal detector with a conveyor belt, a walkthrough metal detector, a gas ionization explosives detector, and a weapons depository unit located in the interior of the inner scanning chamber;

said x-ray metal detector having material capture capability;

said inner storage chamber further comprising an air conditioning unit and a sedation dispenser containing sedation material;

said inner storage chamber further comprising an enclosure with ports to access the inner scanning chamber by which said sedation dispenser can pump sedation material from the storage chamber into said inner scanning chamber;

said entrance door and said exit door further comprising baffles above said entrance door and said exit door for the removal of sedation material;

wherein said metal detector is positioned in said inner scanning chamber such that a user would need to walk through said metal detector to go from the entrance door to the exit door;

having a user enter said entering into said safety enclosure;

wherein said entrance and exit doors are locked when said user enters into the inner scanning chamber;

having said user pass through said metal detector scan;

having said user scanned by said gas ionization explosives detector;

wherein a user maybe be confronted with said sedation material when released into said inner scanning chamber if said user fails said metal detector scan; and wherein a user maybe be confronted with said sedation material when released into said inner scanning chamber if said user fails said gas ionization explosive detector;

having user that is not confronted with sedation materials leave the safety enclosure through the exit door.

10. The method of claim 9 further comprising the step of;

placing an object to be scanned on said conveyor belt to be run through said x-ray metal detection machine; furthermore, if said object is a weapon or a bomb it is captured in said x-ray machine.

11. The method of claim 9 further comprising the step of;

detecting a weapon by one or more of the following, in combination or individually; said x-ray detector, said metal detector, or said gas ionization explosives detector;

releasing said sedation material into the inner scanning chamber therein rendering a user incapacitated.

12. The method of claim 9 further comprising the step of;

detecting a bomb by one or more of the following, in combination or individually: said x-ray detector, said metal detector, or said gas ionization explosives detector, releasing said sedation material into the inner scanning chamber therein rendering a user incapacitated.

13. The method of claim 9 further comprising the step of;

detecting a gun by one or more of the following, in combination or individually: said x-ray detector, said metal detector, or said gas ionization explosives detector;

releasing said sedation material into the inner scanning chamber therein rendering a user incapacitated.

14. The method of claim 9 further comprising the step of;

including on said walled enclosure with a frame further closing baffles located above said entrance and said exit doors to allow air in or to prevent gas from escaping said enclosure.

15. The method of claim 9 further comprising the step of;

attaching to said walled enclosure with a frame a ceiling attached to said walled enclosure with a frame.

16. The method of claim 9 further comprising the step of;

attaching to said ceiling a first exhaust fan attached near said exit door and a second exhaust fan located near said entrance door, a upper tube and a lower tube connected to said sedation materials container; and pumping sedation materials through said first and second exhaust fans through said upper tube, through said lower tube and into said sedation materials container.

17. A security scanning enclosure comprising:

a walled enclosure with a frame with impact resistant walls, an entrance door and exit door;

said walled enclosure with a frame further comprising;

remote cameras capable of transmitting video feed attached to the interior of said walled enclosure with a frame an inner scanning chamber and inner storage chamber with said storage chamber located interior to the inner scanning chamber;

said inner scanning chamber wherein said entrance door and said exit door are located on opposite ends of said inner scanning chamber;

said inner scanning chamber further comprising an x-ray metal detector with a conveyor belt, a walkthrough metal detector, a gas ionization explosives detector, and a weapons depository unit located in the interior of the inner scanning chamber;

said x-ray metal detector having material capture capability;

said inner storage chamber further comprising an air conditioning unit and a sedation dispenser containing sedation material;

said inner storage chamber further comprising an enclosure with ports to access the inner scanning chamber by which said sedation dispenser can pump sedation material from the storage chamber into said inner scanning chamber;

said entrance door and said exit door further comprising baffles above said entrance door and said exit door for the removal of sedation material;

wherein said metal detector is positioned in said inner scanning chamber such that a user would need to walk through said metal detector to go from the entrance door to the exit door;

wherein said entrance and exit doors are locked when said user enters into the inner scanning chamber; and wherein a user maybe be confronted with said sedation material when released into said inner scanning chamber.

18. The security scanning enclosure of claim 17 wherein;

a user may place an object to be scanned on said conveyor belt to be run through said x-ray metal detection machine; furthermore, if said object is a weapon or a bomb it is captured in said x-ray machine.

19. The security scanning enclosure system of claim 17 wherein;
if a weapon is detected by one or more of the following, in combination or individually:
said x-ray detector, said metal detector, or said gas ionization explosives detector;
said sedation material is released in to the inner scanning chamber therein rendering a user incapacitated.

20. The security scanning enclosure of claim 17 wherein;
if a bomb is detected by one or more of the following, in combination or individually; said x-ray detector, said metal detector, or said gas ionization explosives detector;
said sedation material is released in to the inner scanning chamber.

21. The security scanning enclosure of claim 17 wherein;
if a gun is detected by one or more of the following, in combination or individually: said x-ray detector, said metal detector, or said gas ionization explosives detector;
said sedation material is released in to the inner scanning chamber.

22. The security scanning enclosure of claim 17 wherein;
said walled enclosure with a frame further comprises closing baffles located above said entrance and said exit doors to allow air in or to prevent gas from escaping said enclosure.

23. The security scanning enclosure of claim 17 wherein;
said walled enclosure with a frame further comprises a ceiling attached to said walled enclosure with a frame.

24. The security scanning enclosure of claim 17 where in;
said ceiling has a first exhaust fan attached near said exit door and a second exhaust fan located near said entrance door, a upper tube and a lower tube connected to said sedation materials container; and
wherein said first and second exhaust fans can pump sedation materials through said upper tube, through said lower tube and into said sedation materials container.

* * * * *